(12) United States Patent
Saidi et al.

(10) Patent No.: US 8,466,134 B1
(45) Date of Patent: *Jun. 18, 2013

(54) AQUEOUS COMPOSITIONS CONTAINING CORTICOSTEROIDS FOR NASAL AND PULMONARY DELIVERY

(75) Inventors: Zahir Saidi, Cenon (FR); Boris Klyashchitsky, Wilmington, DE (US)

(73) Assignee: Athena Neurosciences, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/019,100

(22) PCT Filed: Jun. 24, 1999

(86) PCT No.: PCT/US99/14351
§ 371 (c)(1),
(2), (4) Date: Aug. 21, 2003

(87) PCT Pub. No.: WO00/00181
PCT Pub. Date: Jan. 6, 2000

Related U.S. Application Data

(63) Continuation-in-part of application No. 09/105,838, filed on Jun. 26, 1998, now Pat. No. 6,241,969.

(51) Int. Cl.
*A01N 45/00* (2006.01)
*A61K 31/56* (2006.01)
*A61K 31/58* (2006.01)
*C07D 311/00* (2006.01)

(52) U.S. Cl.
USPC .......................... 514/170; 514/172; 549/410

(58) Field of Classification Search
USPC ........................................................ 514/170
See application file for complete search history.

(56) References Cited

U.S. PATENT DOCUMENTS

| | | | |
|---|---|---|---|
| 4,073,943 A | 2/1978 | Wretlind et al. | 424/358 |
| 4,299,828 A * | 11/1981 | Wang et al. | 514/174 |
| 4,567,161 A | 1/1986 | Posanski et al. | 514/23 |
| 4,782,047 A | 11/1988 | Benjamin et al. | 514/174 |
| 5,023,271 A | 6/1991 | Vigne et al. | 514/458 |
| 5,192,528 A | 3/1993 | Radhakrishnan et al. | 424/45 |
| 5,208,226 A | 5/1993 | Palmer | 514/171 |
| 5,292,499 A | 3/1994 | Evans et al. | 424/45 |
| 5,444,041 A | 8/1995 | Owen et al. | 514/2 |
| 5,474,759 A | 12/1995 | Fassberg et al. | 424/45 |
| 5,478,860 A | 12/1995 | Wheeler et al. | 514/449 |
| 5,496,811 A | 3/1996 | Aviv et al. | 514/78 |
| 6,193,985 B1 * | 2/2001 | Sonne | 424/400 |

FOREIGN PATENT DOCUMENTS
CA  2083927  12/1993

OTHER PUBLICATIONS

Bochner et al., "Immunological Aspects of Allergic Asthma," *Annu. Rev. Immunol.* 12, 295-335 (1994).
Brain, et al., "Aerosols: Basics and Clinical Considerations," *Bronchial Asthma*, Second Edition, Weiss, E.B. et al., (eds.), Little, Brown and Company, 594-603 (1985).
Eastman Chemical Company, "Eastman Vitamin E TPGS: Properties and Applications," *Pharmaceutical Ingredients*, 1-21 (Oct. 1996).
Goodman & Gilman's, "The Pharmacological Basis of Therapeutics," Ninth Edition, McGraw-Hill, 662-664, 666-667, 1470-1471, 1473, 1480 (1996).
Klyashchitsky et al., "Drug Delivery Systems for Cyclosporine: Achievements and Complications," *J. Drug Targeting*, 5(6), 443-458 (1998).
Klyashchitsky et al.,"Nebulizer-Compatible Liquid Formulations for Aerosol Pulmonary Delivery of Hydrophobic Drugs: Glucocorticoids and Cyclosporine," *J. Drug Targeting*, 7(2), 79-99 (1999).
Ly et al., "Evaluation and Application of Hydrophilic Tocopherol Polyethylene Glycol Derivatives as Enhancers of Drug Solubility," College of Pharmacy and Allied Health Professions, St. John's University, Jamaica, NY, Presentation ID: 3419, Nov. 5, 1997, 1 page summary.
Ly, et al., "Evaluation of (+)-α-Tocopherol Polyethylene Glycol 1000 (TPG) as an Enhancer of Drug Solubility in Aqueous Solution" *Proc. 2nd World Meeting APGI/APV*, Paris, May 25/28, 1-2 (1998).
Pavord et al., "Pharmacokinetic Optimization of Inhaled Steroid Therapy in Asthma," *Clin. Pharmacokinet.*, 25(2), 126-135 (1993).
Schreier et al., "Pulmonary Delivery of Liposomes," *J. Control. Release*, 24, 209-223 (1993).
Waldrep, et al., "High dose Cyclosporin A and Budesonide-liposome aerosols," *Intl. J. Pharm.* 152(1), 27-36 (1997).
Waldrep, et al., "Nebulized Glucococorticoids in Liposomes: Aerosol Characteristics and Human Dose Estimates," *J. Aerosol Medicine*, 7(2), 135-145 (1994).

* cited by examiner

*Primary Examiner* — Sreeni Padmanabhan
*Assistant Examiner* — Layla Soroush
(74) *Attorney, Agent, or Firm* — Fox Rothschild LLP

(57) ABSTRACT

The present invention provides compositions containing corticosteroid compounds as active agents for the treatment of ailments and diseases of the respiratory tract, particularly the lungs, by way of nasal and pulmonary administration. The corticosteroid compounds are present in a dissolved state in the compositions. The compositions can be formulated in a concentrated, essentially non-aqueous form for storage or in a diluted, aqueous-based form for ready delivery. In a preferred embodiment, the corticosteroid composition contains an ethoxylated derivative of vitamin E and/or a polyethylene glycol fatty acid ester as the high-HLB surfactant present in the formulation. The compositions are ideally suited for inhaled delivery with a nebulizer or for nasal delivery.

13 Claims, No Drawings

AQUEOUS COMPOSITIONS CONTAINING CORTICOSTEROIDS FOR NASAL AND PULMONARY DELIVERY

CROSS-REFERENCES TO RELATED APPLICATIONS

This application is a National Stage Entry of International Application No. PCT/US99/14351, filed Jun. 24, 1999, which is a continuation-in-part of U.S. application Ser. No. 09/105,838, filed Jun. 26, 1998, now U.S. Pat. No. 6,241,969.

FIELD OF THE INVENTION

The present invention relates to pulmonary drug delivery compositions useful for the inhaled administration of corticosteroid compounds and the method of their administration. The delivery compositions are useful for the treatment of ailments and diseases of the lungs. Similar corticosteroid compositions may be used for nasal delivery.

BACKGROUND OF THE INVENTION

Delivery of therapeutic compounds directly to affected lung tissues has several advantages. The drug reaches the target tissue without first entering the systemic circulation and being subjected to dilution by the blood, binding to blood components, or metabolism by the liver and excretion by the kidneys. A high local concentration of drug can be achieved in the lungs while the systemic concentration is kept below that likely to cause adverse side effects. In addition, the apical side of the lung tissue—the side exposed directly to inspired air—can be treated with compounds that might not readily cross the endothelium or epithelium, which form barriers between the apical surface and the blood plasma. Similar considerations apply to the tissues lining the nasal passages and sinus cavities.

Several means have been developed to deliver compounds directly to the passages of the lung or nose. The most common form, especially for water-insoluble drugs, is a powder suspension that is propelled into the mouth while the patient inhales. Propulsion is accomplished by use of pressurized gas or by any of a variety of mechanical means of entraining a fine powder into a gas or air stream. Common devices for this purpose include metered dose inhalers (MDIs), turbo inhalers, and dry powder inhalers. Each of these uses a different means of propulsion; however, a common characteristic is that once the therapeutic drug leaves the device it is, or becomes, a fine powder. In an MDI, the drug may be suspended or solubilized in a non-aqueous propellant, which is typically a chlorofluorocarbon or fluorinated hydrocarbon that is a liquid under pressure at room temperature. In turbo inhalers and dry powder inhalers, the drug is present in the form of a micronized powder.

The particle size distribution of the aerosolized drug compositions is very important to the therapeutic efficacy of the drug when delivered by inhalation. Studies of inhaled aerosols indicate that particles or droplets of greater than about 5 micrometers in mean aerodynamic diameter are effectively excluded from entry into the lungs and are captured in the nasal passages or throat and swallowed instead. Thus, the drug compounds delivered by these devices must be formulated in such a way that the mass median aerodynamic diameter (MMAD) is below 5 micrometers. In addition, even smaller particle sizes, on the order of 0.5 to 2.5 micrometers, are needed if the drug is to reach the alveolar sacs deep in the lungs. However, particles with aerodynamic diameter less than about 0.5 micrometers are likely to be exhaled before the drug is totally deposited on the lung surface.

Additional considerations for the use of powder-type drug delivery devices for inhalation include the limited amount of drug that can be contained in one or two puffs from the device and the need for the user to skillfully coordinate hand activation of the device with inhalation. This latter limitation is particularly important for those patients who are disabled, children, or elderly.

Nebulizers offer an alternative method of administering therapeutic agents to the lungs. These devices work by means of an air jet or an ultrasonic pulse that is applied to a solution producing a fine mist. Therapeutic agents dissolved or suspended in the solution can be incorporated into the mist. The patient then breathes the mist in and out over the course of several minutes of treatment, during which 1 to 3 mL of the drug formulation is typically nebulized. Considerations of particle size mentioned above also apply to the droplet size of the mists. However, it is possible to rebreathe a portion of the mist during several minutes of treatment and increase the capture of the fine droplet fraction that can penetrate the lung most deeply. In addition, there is no need for coordination between hand action and breathing, making the nebulizer easier to use for patients. It may be possible, in some cases, to administer drugs not soluble in aqueous solution by nebulizing them in suspension. However, the droplet size of nebulized drug-containing suspensions cannot be smaller than that of the suspended particles. Therefore, the finer droplets produced from these systems would not contain any drug.

Thus, one limitation of nebulized formulations is that they are most suitable for those drug compounds that are sufficiently water soluble such that a therapeutic dose of the drug can be dissolved in from 1 to about 3 mL of aqueous solution. One way around this limitation is to formulate with polar organic solvents or aqueous solutions thereof. However, few organic solvents can be safely inhaled for prolonged periods. Most organic solvents that are currently approved for use in inhalation devices are propellants, such as chlorofluorocarbons (CFCs), which will soon be eliminated from manufacturing for environmental reasons, or the newer hydrofluorocarbons and low boiling hydrocarbons, all of which are expected to evaporate prior to penetrating the lungs. Such solvents can evaporate rapidly during nebulization and leave the drug behind in the device or in large particles that would be likely to be deposited in the mouth or throat rather than be carried to the lungs. Indeed, MDIs were developed to circumvent such problems.

Another way to overcome the solubility problem of the drug is to blend cosolvents such as ethanol, propylene glycol, or polyethylene glycol with water. However, there are limits to acceptable levels of these cosolvents in inhaled products. Typically, the cosolvents make up less than about 35% by weight of the nebulized composition, although it is the total dose of cosolvent as well as its concentration that determines these limits. The limits are set by the propensity of these solvents either to cause local irritation of lung tissue, to form hyperosmotic solutions which would draw fluid into the lungs, and/or to intoxicate the patient. In addition, most potential hydrophobic therapeutic agents are not sufficiently soluble in these cosolvent mixtures.

Thus, there is a need to develop improved systems that can solubilize water-insoluble drugs for nebulization, and to minimize the levels of cosolvent necessary to accomplish this. The ideal system would have a cosolvent concentration below about 15% and in certain cases below about 5%. It would consist of non-toxic ingredients and be stable for long periods of storage at room temperature. When nebulized, it would produce droplets having an MMAD less than about 5 micrometers.

Droplet size considerations are not as critical for sinus or nasal administration, but it is still important to use safe, non-irritating ingredients. An additional consideration for both nasal and inhaled delivery is that some of the formulation will inevitably be tasted and swallowed. Therefore, acceptable taste and odor must be considered important parameters, especially for nebulized formulations where exposure is prolonged and where pediatric subjects form an important fraction of the probable patient population.

Anti-inflammatory corticosteroids, which are essentially water-insoluble drugs that act on inflammatory cells in the respiratory mucosa, are a type of therapeutic compounds in need of improved inhaled delivery. These steroids are useful in treating a variety of inflammatory diseases including asthma.

Asthma is a chronic obstructive disease of the lower airways. The major clinical and pathological features of asthma are (partially) reversible airflow limitations due to bronchial constriction, bronchial hyperreactivity to noxious stimuli such as allergens or cold air, and inflammation of the airways. Anti-inflammatory corticosteroids are useful in treating this last condition. They are the most effective group of therapeutic agents currently available for treating allergic asthma. The steroids suppress many inflammatory processes including inhibition of eosinophilia, epithelial shedding, and edema. The cellular basis of these actions is under active investigation.

Like other steroid hormone analogs, corticosteroids bind with high affinity to cytoplasmic receptor proteins in target cells. The receptor-steroid complexes migrate to the cell nucleus, where they interact with nuclear chromatin to control gene expression. The receptor binding is saturable and very small amounts of steroid suffice to elicit maximum cellular responses, including suppression of inflammation.

Anti-inflammatory steroids can act systemically as well as locally. Therefore, while systemic administration of anti-inflammatory steroids will diminish airway inflammation in asthmatics, it can also cause such adverse effects as general immunosuppression and imbalances in mineral metabolism. The corticosteroids commonly used in asthma treatment have a high ratio of topical to systemic potency. That is, these corticosteroids are highly active when delivered directly to the site of inflammation but relatively inactive when passed through the systemic circulation. The portion of an inhaled dose which is swallowed and absorbed through the intestine or absorbed through the lung tissue into the circulation is subjected to metabolism by the liver and converted to less active compounds with short half-lives. These metabolites are quickly eliminated from the blood, reducing the incidence of systemic side effects.

Among the most commonly used steroids are aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, mometasone, paramethasone, prednisolone, prednisone, tixocortol, triamcinolone, and others, and their respective pharmaceutically acceptable derivatives, such as beclomethasone diproprionate, dexamethasone 21-isonicotinate, fluticasone propionate, icomethasone enbutate, tixocortol 21-pivalate, triamcinolone acetonide, and others. Fortunately, some of these synthetic steroids have low potentials for systemic absorption because of their unique structures and metabolism.

Corticosteroids have usually been formulated as suspensions of micronized drug powder in chlorofluorocarbon vehicles or with chlorofluorocarbon-free propellants and delivered by metered dose inhaler. The choice of this type of carrier and apparatus was dictated by the fact that corticosteroids are very difficult to stabilize in aqueous media and frequently produce systems that exhibit crystal growth, precipitation, and/or aggregation of suspended or solubilized drug.

Corticosteroids have been formulated in different drug delivery systems for administration to the respiratory tract. U.S. Pat. No. 5,292,499 relates to reverse micelle colloidal dispersions of hydrophilic pharmaceutically active compounds prepared with aerosol CFC propellant formulations useful for topical, endopulmonary, nasal, or inhalation administration.

U.S. Pat. No. 5,208,226 describes the concept of using a novel combination therapy, which has greater efficacy and duration of bronchodilator action than previously known combinations and that permits the establishment of a twice daily dosing regimen. The effective treatment consists of administration of a stimulant bronchodilator, salmeterol, and/or a physiologically acceptable salt thereof, combined with beclomethasone dipropionate in a form suitable for inhalation such as a metered dose inhaler with dry powder or chlorofluorocarbon-containing formulations.

U.S. Pat. No. 5,474,759 discloses aerosol formulations that are substantially free of chlorofluorocarbons, and having particular utility in medicinal applications. The formulations contain a propellant (such as 1,1,1,2,3,3,3-heptafluoropropane), a medium-chain fatty acid propylene glycol diester, a medium-chain triglyceride, optionally a surfactant, and optionally auxiliary agents such as antioxidants, preservatives, buffers, sweeteners and taste masking agents. These formulations are used as carriers for the delivery of inhaled drugs such as albuterol, momestrasone, isoprenaline, disodium cromoglycate, pentamidine, ipratropium bromide, and salts and clathrates thereof.

Recently, several corticosteroid liposomal formulations have been under development. U.S. Pat. No. 5,192,528 discloses the delivery of corticosteroids by inhalation for treating a variety of lung diseases. The carrier consists of an aqueous suspension of sized liposomes containing the drug. This liposome-entrapped drug form is then aerosolized, using a pneumatic nebulizer, to deliver the drug to the lung. Cholesterol and/or cholesterol sulfate can be incorporated into the system to delay the release of corticosteroid from the liposomes in the lung environment. These formulations have many advantages over microcrystalline formulations, including utilization of otherwise water-insoluble materials, sustained pulmonary release, and facilitated intracellular delivery. However, some general problems pertaining to liposomes regarding manufacturing processes, the use of synthetic phopsholipids (such as dilauroylphosphatidylcholine), and the distribution patterns of aerosolized liposomes in the lung may cause difficulties in the wide application of this type of aerosolized formulation.

There are as yet no marketed, commercial liposomal, micellar, or microemulsion formulations available for pulmonary delivery of corticosteroids.

SUMMARY OF THE INVENTION

The present invention provides compositions suitable for administering a therapeutic dose of a corticosteroid to the respiratory tract and methods for the administration of said compositions.

In one embodiment, the corticosteroid composition contains from about 0.1 to about 20 percent by weight of a high-HLB surfactant component (HLB greater than about 10), for example, ethoxylated derivatives of Vitamin E such as tocopheryl polyethylene glycol 1000 succinate ("TPGS"). The HLB, or hydrophilic-lipophilic balance, is a measure on an arbitrary scale of the polarity of a surfactant or mixture of surfactants. For example, TPGS has an HLB between about 15 and 19. Generally, the corticosteroid composition contains the corticosteroid in an amount from about 5 µg/ml to about 1 mg/ml. The composition is aqueous-based, containing at least about 70 weight percent of an aqueous phase that can include buffering, tonicity, taste-masking, and preservation additives.

The corticosteroid composition can also contain one or more pharmaceutically acceptable cosolvents to aid in the processing of the composition and to increase the solubility of the corticosteroid. Such cosolvents include mono- and polyvalent alcohols, such as propylene glycol, ethanol, and polyethylene glycol. Optionally, the corticosteroid compositions also can contain such components as low-HLB surfactants (HLB below about 8) and/or oils. Low-HLB surfactants include phospholipids, medium-chain mono- and diglycerides, and mixtures thereof. Useful pharmaceutically acceptable oils include triglycerides and propylene glycol diesters of medium-chain fatty acids.

DETAILED DESCRIPTION OF THE INVENTION

The present invention provides compositions containing corticosteroid compounds as active agents for the treatment of ailments and diseases of the respiratory tract, particularly the lungs, by way of nasal and pulmonary administration. The compositions can be formulated such that they contain the corticosteroid active agent(s) in a dissolved state. The formulations can be stored either in a concentrated form to be diluted at the time of use or a ready-for-use, diluted state. The present invention also sets forth methods for using the compositions for nasal or inhaled delivery.

The corticosteroid compositions of the present invention are preferably formulated with ethoxylated derivatives of vitamin E as the high-HLB surfactant component. An example of a preferred high-HLB surfactant from this class of surfactants is tocopheryl polyethylene glycol 1000 succinate ("TPGS"). TPGS is commercially available from Eastman Chemical Company as "Vitamin E TPGS", and has been used as a water-soluble Vitamin E supplement for oral ingestion. It is a waxy solid at room temperature and has melting point around 40° C. It has been found that the use of TPGS in corticosteroid compositions is particularly advantageous due to the ability of TPGS to solubilize corticosteroids and to form a stable micellar solution upon dilution in an aqueous phase, and also due to the neutral taste of TPGS when used in a corticosteroid composition that is administered either nasally or by inhalation. Consequently, an embodiment of the present invention that is particularly well suited for ease of manufacturing is one in which the corticosteroid compound is initially dissolved in TPGS to form a "concentrate" that is diluted with an aqueous phase to form the final corticosteroid composition. This composition is a micellar solution because the concentration of TPGS is far above the critical micellar concentration (CMC) of TPGS, which is about 0.02 wt. percent in water at 37° C. This embodiment is easy to manufacture, has a low level of excipients, and has a neutral taste for inhalation delivery.

Compositions designed for inhaled administration have a level of the high-HLB surfactant in the final, diluted corticosteroid composition from about 0.1 to about 20, preferably from about 0.25 to about 15, and more preferably from about 0.5 to about 5, percent by weight. Compositions designed for nasal administration have a level of the high-HLB surfactant in the final, diluted corticosteroid composition from about 1 to about 20, preferably from about 2.5 to about 15 and more preferably from about 5 to about 10, percent by weight.

The corticosteroids that are useful in the present invention generally include any steroid produced by the adrenocortex, including glucocorticoids and mineralocorticoids, and synthetic analogs and derivatives of naturally occurring corticosteroids having anti-inflammatory activity. Examples of corticosteroids that can be used in the compositions of the invention include aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol, triamcinolone, and their respective pharmaceutically acceptable derivatives, such as beclomethasone diproprionate, dexamethasone 21-isonicotinate, fluticasone propionate, icomethasone enbutate, tixocortol 21-pivalate, and triamcinolone acetonide. Particularly preferred are compounds such as beclomethasone diproprionate, budesonide, flunisolide, fluticasone propionate, mometasone and triamcinolone acetonide.

The corticosteroid compound is present in the final, diluted corticosteroid composition designed for inhalation in an amount from about 5 µg/ml to about 5 mg/ml, preferably from about 10 µg/ml to about 1 mg/ml, and more preferably from about 20 µg/ml to about 500 µg/ml. For example, the preferred drug concentration is between about 20 and 100 µg/ml for beclomethasone dipropionate, between about 30 and 150 µg/ml for triamcinolone acetonide, and between about 50 and 200 µg/ml for budesonide, depending on the volume to be administered. By following the preferred methods of the present invention, relatively high solubilities of the corticosteroid can be achieved in an aqueous-based composition. The solubility of the corticosteroid can be greater than about 50, preferably greater than about 75, and more preferably greater than about 100, in some cases greater than about 150 or about 200, µg/ml.

Similarly, the corticosteroid compound is present in the final, diluted corticosteroid composition designed for nasal administration in an amount from about 50 µg/ml to about 10 mg/ml, preferably from about 100 µg/ml to about 2 mg/ml, and more preferably from about 300 µg/ml to about 1 mg/ml. For example, the preferred drug concentration is between about 200 and 900 µg/ml for beclomethasone dipropionate, between about 250 µg/ml and 1 mg/ml for triamcinolone acetonide, and between about 400 µg/ml and 1.6 mg/ml for budesonide, depending on the volume to be administered.

The corticosteroid composition can also contain various excipients that improve the storage stability of the composition, but which do not significantly affect the overall efficacy of the composition in its freshly prepared state. Such excipients include buffers, osmotic (tonicity-adjusting) agents, low toxicity antifoaming agents, and preservatives.

Buffers are used in the present compositions to adjust the pH to a range of between about 4 and about 8, preferably between about 4.5 to about 7, and more preferably between about 5 and about 6.8. It has been found that for certain corticosteroids the pH can be lowered further to enhance the stability of the aqueous compositions. For example, in certain formulations, the preferred pH range is between about 3 and about 8, preferably between about 3.2 and about 6.5, and more preferably between about 3.5 and about 6. Budesonide is an example of a corticosteroid that has shown superior stability at these lower pH ranges. The buffer species may be any pharmaceutically approved buffer providing the aforementioned pH ranges, such as citrate, phosphate, malate, etc. A preferred buffer solution is citrate buffer with concentrations from about 0.0005 to about 0.05 M, preferably from about 0.001 to about 0.025 M, and more preferably from about 0.005 to about 0.02 M.

The osmotic agent can be used in the compositions to enhance the overall comfort to the patient upon delivery of the corticosteroid composition. It is preferred to adjust the osmolality of the composition to about 280-300 mOsm/kg. Such agents include any low molecular weight water-soluble species pharmaceutically approved for pulmonary and nasal delivery such as sodium chloride and glucose.

Preservatives can be used to inhibit microbial growth in the compositions. The amount of preservative is generally that which is necessary to prevent microbial growth in the composition for a storage period of at least six months. Examples of pharmaceutically acceptable preservatives include the parabens, benzalkonium chloride, thimerosal, chlorobutanol, phenylethyl alcohol, benzyl alcohol, and potassium sorbate.

Corticosteroid compositions that contain the high-HLB surfactant can be prepared as follows. TPGS will be used as the representative high-HLB surfactant for illustrative purposes. First, the TPGS may be heated to a temperature of at least about 40° C., preferably at least about 45° C., and generally about 45-60° C. The appropriate quantity of the corticosteroid compound is then dissolved in the molten TPGS at the same temperature, thus forming the concentrated corticosteroid composition. To achieve the final, diluted corticosteroid composition, the molten concentrated corticosteroid composition is slowly added under continuous stirring to an aqueous phase. The aqueous phase is preferably water containing the additives necessary to adjust the pH and tonicity, and preservatives if the formulation is intended for multiple use. It is preferred that the aqueous phase be heated prior to the addition of the molten corticosteroid concentrate to aid in dispersion. Generally, the aqueous phase should be heated to about 55-85° C., more preferably from about 60-70° C.

It is preferred that the diluted corticosteroid composition be formulated by first dissolving the drug in the molten TPGS and then dispersing this concentrate in the aqueous phase. If the drug is added to a prediluted mixture of TPGS and aqueous phase, it may not be possible to achieve the final desired concentration of the drug in a dissolved state. To ensure that the drug is solubilized and stable in the diluted composition, it is preferred that the level of the drug in the concentrated composition be from about 1 to about 30 mg/ml, preferably from about 2 to about 20 mg/ml, and more preferably from about 2 to about 10 mg/ml prior to dilution. The level of water in the concentrated corticosteroid composition should be below 5% by weight, preferably below 2% by weight, and more preferably below 1% by weight, and in general, it is advantageous not to add any water to the concentrated corticosteroid composition.

The aqueous phase, which is composed of water and optionally buffering, tonicity, and/or preservation additives, is present in the diluted corticosteroid compositions containing TPGS in an amount of at least about 70, preferably at least about 80, more preferably at least 90, and even more preferably at least about 95, percent by weight. The various other additives, such as buffers, tonicity adjusting agents, and preservatives, are preferably blended into the compositions as part of the aqueous phase, and the use of the term "aqueous phase" is intended to include such components, if used.

It has been found that the inclusion of any one of a group of cosolvents in these TPGS corticosteroid compositions can aid in the processing of the compositions and in the solubilizing of the drug. Preferred cosolvents include mono- and polyvalent alcohols, such as propylene glycol, ethanol, glycerol, glycofurol (available as Tetraglycol from Sigma), ethoxydiglycol (available as Transcutol from Gattefosse), and polyethylene glycol (PEG) having an average molecular weight between about 200 and 4000, preferably between 200 and 1000, more preferably PEG 400, and combinations thereof. The cosolvents can be present individually in the final, diluted corticosteroid compositions in concentrations from about 0.1 to about 20, preferably from about 0.25 to about 15, more preferably from about 0.5 to about 5, and even more preferably from about 0.5 to about 2.5, percent by weight. The total level of cosolvents combined in the final, diluted corticosteroid compositions is from about 0.1 to about 20, preferably from about 0.25 to about 15, more preferably from about 0.5 to about 10, and even more preferably from about 0.5 to about 5, percent by weight.

When preparing the corticosteroid compositions, the cosolvents can be added to the molten TPGS, to the TPGS/drug concentrate, or to the aqueous phase in which the TPGS/drug concentrate will be dispersed. Any way, stable diluted corticosteroid compositions can be produced with the drug in a dissolved state. If the cosolvents are blended with the molten TPGS prior to the addition of the drug, the temperature of this concentrate can then be reduced during the dissolution process. In general, the temperature of the TPGS/cosolvent mixture can be maintained below about 50° C., preferably below about 45° C., in order to dissolve the drug. In some cases, such as when a volatile cosolvent like ethanol is used, no heating is necessary to achieve dissolution. In addition, when the concentrated composition contains a cosolvent, it is not necessary to heat the aqueous phase used as the dilution medium to form the diluted corticosteroid composition.

Alternatively, the drug can be first dissolved in the cosolvent or blend of cosolvents at 20-50° C. and then that solution is blended with the molten TPGS to form the concentrated corticosteroid composition.

Other preferred high-HLB surfactants that can be used in place of, or in admixture with, ethoxylated derivatives of vitamin E are polyethylene glycol fatty acid esters. The fatty acid moiety preferably has from about 8 to about 18 carbon atoms. A preferred polyethylene glycol fatty acid high-HLB surfactant product is "Solutol HS-15," available from BASF Fine Chemicals. Solutol HS-15 is a mixture of polyethyleneglycol 660 12-hydroxystearate (70%) and polyethylene glycol (30%). It is a white paste at room temperature that becomes liquid at about 30° C. and has an HLB of about 15. Aqueous solutions of this surfactant, like those of TPGS, have a neutral taste. Similar preferred manufacturing processes and behavior regarding the dissolution of drugs, dilution methods, and the addition of cosolvents apply to Solutol HS-15 as those mentioned above for TPGS.

The corticosteroid compositions can contain other high-HLB surfactants, such as ethoxylated hydrogenated castor oil (Cremophor RH40 and RH60, available from BASF), tyloxapol, sorbitan esters such as the Tween series (from ICI Surfactants) or the Montanox series (from Seppic), etc. The corticosteroid compositions preferably contain either, or both, of the ethoxylated derivatives of vitamin E or the polyethylene glycol fatty acid esters as all or part of the high-HLB surfactant component, and in general the sum of these two types of surfactants will account for at least 50%, preferably at least 75%, and more preferably at least 90% by wt. of the high-HLB surfactant component.

Optionally, low HLB surfactants, having an HLB value below about 8, can also be used in the present invention. Examples of such low HLB surfactants include phospholipids, such as phosphatidylethanolamine, phosphatidylcholine, and phosphatidylinositol; and medium-chain mono- and diglycerides, i.e., mono- and di-glycerides of $C_8$ to $C_{12}$ fatty acids, and mixtures thereof. The low HLB surfactants can be used in general at levels from about 0.1 to about 3 percent by weight in the diluted composition.

Optionally, an oil can also be incorporated into the compositions. Examples of pharmaceutically acceptable oil compounds include triglycerides and propylene glycol diesters of $C_8$ to $C_{12}$ fatty acids such as the Captex series available from Abitec. Oils can be used in general in levels from about 1 to about 30 percent by weight in the concentrated compositions and from about 0.1 to about 3 percent by weight in the diluted composition.

It is necessary to add the drug to the compositions containing high-HLB and low HLB surfactants, and/or cosolvents, and/or the oil compounds, to form the concentrated corticosteroid composition prior to dilution with the aqueous phase.

The diluted corticosteroid compositions using high-HLB surfactants such as TPGS or Solutol HS-15 to solubilize the drug are believed to be micellar compositions. This belief is based on the fact that the critical micelle concentration for both TPGS and Solutol HS-15 is about 0.02% by weight at 37° C., which is below their concentration in the diluted corticosteroid compositions. If an oil component is present with or without a low HLB surfactant, an oil-in-water (o/w) microemulsion may be formed as the diluted corticosteroid composition.

The aforementioned diluted compositions can be administered to the body in the form of an aerosol. For administration to the respiratory tract, particularly the lungs, a nebulizer is used to produce appropriately sized droplets. Typically, the particle size of the droplet produced by a nebulizer for inhalation is in the range between about 0.5 to about 5 microns. If it is desired that the droplets reach the lower regions of the respiratory tract, i.e., the alveoli and terminal bronchi, the preferred particle size range is between about 0.5 and about 2.5 microns. If it is desired that the droplets reach the upper respiratory tract, the preferred particle size range is between 2.5 microns and 5 microns. The nebulizer operates by directing pressurized air to fluidize the droplets of the diluted corticosteroid composition, which resultant aerosol is directed through a nozzle and subsequently through a baffle system that removes larger particles.

For the treatment of bronchial constriction, the diluted corticosteroid composition is prepared as described above. The corticosteroid for such treatment is preferably either beclomethasone dipropionate, betamethasone, budesonide, dexamethasone, flunisolide, fluticasone propionate, or triamcinolone acetonide, and is formulated in the concentrations set forth above. The daily dose of the corticosteroid is generally about 0.4 to 2 mg, depending on the drug and the disease, in accordance with the Physician's Desk Reference.

EXAMPLES

Various embodiments of the present invention are illustrated by the following examples, which should not be intended to limit the scope of the invention. The compositions of Examples 1, 2, 3, and 5 are suitable for inhalation via nebulization and the composition of Example 4 is suitable for nasal administration.

Example 1

The glucocorticoid beclomethasone dipropionate monohydrate was dissolved in premelted (50° C.) TPGS at concentrations of 2.8 and 6.3 mg per gram. These concentrates were kept at 50° C. during the entire solubilization process, which was about 15 min. While in this molten form, the concentrates were diluted at various volume ratios from 1:10 to 1:100 in various aqueous solutions such as hot (80° C.) deionized water, saline, malate buffer, citrate buffer, phosphate buffer, and 5% solutions of propylene glycol, PEG 200, or PEG 400 in any of the above. These diluted compositions were blended until any gel that may have formed when the TPGS concentrate came into contact with the aqueous phase was completely dispersed. Transparent, physically stable, diluted corticosteroid compositions without any precipitates were obtained containing about 28 to 420 μg/ml beclomethasone dipropionate. The diluted corticosteroid compositions were sterilized by passing them through a 0.22 micron sterile filter.

Example 2

Beclomethasone dipropionate monohydrate (4.2 mg) was dissolved in 995.8 mg of a binary liquid mixture of TPGS and ethanol (1:1 weight ratio) by briefly mixing at room temperature to form a concentrated corticosteroid composition. The concentrate was diluted 1:100 by volume in solutions of 5 wt. % PEG 400 in either deionized water, saline, or 20 mM malate, citrate, or phosphate buffer, by mixing for several minutes at room temperature. The resulting optically transparent, diluted corticosteroid compositions contained about 42 μg beclomethasone dipropionate per ml. The diluted corticosteroid compositions were sterilized by passing them through a 0.22 micron sterile filter.

The same concentrated corticosteroid composition was also diluted 1:50 by volume in the above-mentioned aqueous phases, and resulted in final formulations containing about 84 μg beclomethasone dipropionate per ml. These diluted formulations were physically and chemically stable for over a year at 5° C., 25° C./60% RH and 40° C./75% RH.

Example 3

Several corticosteroids—beclomethasone dipropionate, budesonide, and triamcinolone acetonide—were dissolved in binary mixtures of TPGS and a cosolvent selected from the group of ethanol, propylene glycol, PEG 200 and PEG 400. The weight ratio of TPGS to cosolvent was 1:1, and the resulting drug concentrations were between 1.4 and 4.0 mg/gram. It was necessary to heat the TPGS/propylene glycol and the TPGS/PEG mixtures to approximately 45° C. for several minutes in order to dissolve the drugs, but dissolution could be achieved in the TPGS/ethanol mixture at room temperature. The concentrates were diluted 1:50 by volume in an aqueous phase (5% wt. PEG 400 in deionized water) resulting in clear solutions containing from 28 μg to 80 μg per mL. The diluted corticosteroid compositions were sterilized by passing them through a 0.22 micron sterile filter.

Example 4

The composition of this example is suitable for nasal administration. Beclomethasone dipropionate monohydrate (2.8 mg) was dissolved in 997.2 mg of a 2:1 w/w mixture of PEG 200 and TPGS and then diluted (1:6.65 by volume) with deionized water. The final transparent solution contained 420 µg of beclomethasone dipropionate per mL of solution. The composition of the formulation is given below. The tonicity can be adjusted to about 300 mOsm/kg by the addition of glucose or sodium chloride.

| Component | Weight Percent Concentrate Mixture | Wt/Vol. Percent After 1:6.65 Dilution |
|---|---|---|
| TPGS | 33.24 | 5 |
| PEG 200 | 66.48 | 10 |
| Beclomethasone dipropionate | 0.28 | 0.042 |
| Deionized water | — | q.s. |

The diluted corticosteroid compositions were sterilized by passing them through a 0.22 micron sterile filter.

Example 5

In order to assess the stability profiles of some of the corticosteroid compositions described in this invention, four formulations were made with the weight compositions given in the following table.

| Component | Form. 1 | Form. 2 | Form. 3 | Form. 4 |
|---|---|---|---|---|
| Beclomethasone dipropionate | 42 µg/g | 42 µg/g | 42 µg/g | 42 µg/g |
| TPGS | 1% | 1% | 0.5% | 0.5% |
| Polyethylene glycol 400 | ... | 1% | 5% | 5% |
| Ethyl Alcohol (190 Proof) | ... | ... | 0.5% | 0.5% |
| Deionized Water | q.s. | q.s. | q.s. | ... |
| 0.9% NaCl Solution | ... | ... | ... | q.s. |

Formulations were stored in glass vials and blow-molded polyethylene ampules for the duration of the study. Various tests were used to assess the physical and chemical stability of the corticosteroid compositions given above.

Size and distribution of the dispersed material droplets in the aqueous solution of the above compositions were determined using a quasi-elastic light scattering technique. The experimental equipment consisted of a BI-200SM Goniometer and BI9000AT Digital Correlator from Brookhaven Instrument Corporation, and a Thorn EMI Electron tube for detection powered by a high voltage power supply, delivering 2000 volts, from Bertan Associates. A helium-neon laser from Spectra Physics was the light source, with a wavelength of 632.8 nm. The droplet size of the dispersed phase in all formulations before nebulization was about 10 nm, and remained constant for the duration of the study.

The MMAD and the corresponding geometric standard deviation (GSD) of the nebulized corticosteroid compositions were determined at time zero of the study. Saline was used as a reference. The experiments were done using a system consisting of a Proneb compressor and a Pari LC Plus Reusable Nebulizer (Pari Respiratory Equipment, Inc., Richmond, Va.) equipped with an adapted mouthpiece, connected in series with an Andersen cascade impactor (Andersen Airsampler Inc., Atlanta, Ga.). A vacuum pump was connected to the outlet of the cascade impactor, and between them was an air flow controller which indicated a flow of about 28.3 L/min. A cascade impactor is a mechanical model of human lung, containing seven stages and a filter before the outlet, which represent increasing depths of penetration. The amount of excipients deposited on each plate was determined by the increase in the plate dry weight. Analogous results were obtained when determining the MMAD from the drug mass on each plate. This showed that the drug travels in same manner as the excipients.

| Formulation | MMAD (μm) | % GSD |
|---|---|---|
| 1 | 2.939 | 2.81 |
| 2 | 2.294 | 2.46 |
| 3 | 2.795 | 2.48 |
| 4 | 2.165 | 2.42 |
| Saline | 2.216 | 2.16 |

Analysis for the corticosteroid content and degradation products in the above compositions was performed by HPLC. A Shimadzu LC 10A was used with a Supelcosil LC-318 column and UV/VIS detector monitoring absorbance at a wavelength of 254 nm. The isocratic method used 60% acetonitrile in deionized water at a flow rate of about 1.5 mL/min for 15 min. Visual examinations of the corticosteroid compositions under crossed polarized light films and by the naked eye were made on a weekly basis. These examinations were done in order to observe over time whether there was any phase separation, drug precipitate, turbidity or change in color. Results of the stability study at 40° C./75% RH after 12 weeks are shown below. From these data it can be concluded that the tested formulations are physically stable, meaning that there was no phase separation or precipitation of the drug under stressed conditions. No degradation of the corticosteroid was observed. Similar results were obtained from samples which were stored at 5° C. and 25° C.

| Formulation | Drug content, t = 0, μg/mL | Drug content, t = 12 wk μg/mL (%) | |
|---|---|---|---|
| | | glass vials | LDPE ampules |
| 1 | 43.09 | 45.08 (104.6) | 45.49 (105.6) |
| 2 | 42.55 | 43.80 (102.9) | 44.32 (104.2) |
| 3 | 41.96 | 42.91 (102.3) | 43.06 (102.6) |
| 4 | 41.31 | 41.55 (100.6) | 41.26 (99.9) |

Examples 6 through 8 describe additional compositions suitable for inhalation.

Example 6

These budesonide formulation compositions are suitable inhaled delivery compositions:

| Component | Formulation 1 | Formulation 2 |
|---|---|---|
| Budesonide | 100 μg/g | 100 μg/g |
| TPGS | 1% | 1% |
| Propylene glycol | 1.72% | — |
| Polyethylene glycol 400 | — | 1% |
| Sodium chloride | — | 0.65% |
| Citrate Buffer | 97.27% | 97.34% |

Formulation 1 was prepared as the follows: a mixture of melted TPGS and propylene glycol in a weight ratio of 1:1.72 was first prepared at 45 to 50° C., then the resulting liquid concentrate was cooled to ambient temperature. Budesonide was then added and dissolved at ambient temperature. The concentrate was diluted at room temperature in 20 mM citrate buffer at pHs of 3.5, 4.0 and 4.5.

Formulation 2 was prepared similarly to formulation 1 with a mixture of melted TPGS and PEG 400 with a weight ratio of 1 to 1. The budesonide was dissolved by stirring at 35 to 40° C. The mixture was slightly warmed to reduce viscosity. Alternatively, budesonide will dissolve at room temperature by using appropriate mechanical mixing equipment. The resulting concentrate was then diluted at ambient temperature into solutions of 20 mM citrate buffer with the above pHs containing sodium chloride to adjust the tonicity.

After dilution all samples were sterilized by filtering them through a 0.2 μm Millipore sterile filters and placed in sterile low density polyethylene plastic vials. These formulations were kept in humidity and temperature controlled chambers at 5° C. 25° C./60% RH and 40° C./75% RH (where RH is the relative humidity). The % recovery after 13.5 weeks from time zero is presented for each formulation and storage condition, in the following table:

|     | Formulation 1 | | | Formulation 2 | | |
| --- | --- | --- | --- | --- | --- | --- |
| pH | 5° C. | 25° C. | 40° C. | 5° C. | 25° C. | 40° C. |
| 3.5 | 100.2 | 98.7 | 95.2 | 101.0 | 100.1 | 95.2 |
| 4.0 | 98.9 | 98.5 | ND | 99.1 | 100.0 | 94.8 |
| 4.5 | 99.8 | 100.0 | ND | 99.7 | 99.0 | ND |

ND designates "not determined," as these were below 95%.

Example 7

Budesonide compositions containing 0.5 mg/mL budesonide in the final concentrations were prepared and diluted in citrate buffer as described in example 6. The formulations were:

| Component | Formulation 1 | Formulation 2 |
| --- | --- | --- |
| Budesonide | 500 μg/g | 500 μg/g |
| TPGS | 3% | 3% |
| Propylene glycol | 1.5% | — |
| Polyethylene glycol 400 | — | 3% |
| Phenyl ethyl alcohol | 0.25% | 0.25% |
| Benzalkonium chloride | 0.02% | 0.02% |
| Sodium chloride | — | 0.35% |
| Citrate buffer | 95.18% | 93.33% |

The potential of formulation 1 to deliver therapeutic doses of budesonide by inhalation was demonstrated in the following studies. The MMADs, GSDs, and the respirable fractions of the formulations were determined by nebulizing each for 15 minutes, using a Pari ProNeb compressor nebulizer, and entraining the nebulized mist through an Andersen cascade impactor (Andersen Air Samplers, Inc., Atlanta, Ga.) as described in Example 5. The Respirable Fraction is the ratio, given as a percent, of the drug deposited in stage 2 or lower in the cascade impactor to the total amount entering the device and provides an estimate of the fraction of the drug likely to reach the deeper areas of the lungs.

|     | Formulation 1 (Budesonide 500 μg/g- 3% TPGS) | Formulation 2 of Ex. 6 (Budesonide 100 μg/g -1% TPGS) |
| --- | --- | --- |
| MMAD (μm) | 2.15 | 2.26 |
| GSD | 2.75 | 2.76 |
| Respirable Fraction (%) | 63.3 | 61.8 |

Both the MMAD data and the respirable fraction data support the utility of these formulations for delivery of budesonide to the lung by way of inhalation. These formulations can also be used for nasal delivery using a spray device, preferably with the preservatives.

Example 8

The formulations described in Examples 6 and 7 were also prepared using lower buffer concentrations of 10 mM, 5 mM, and 1 mM with similar stability results. However, using buffer concentrations of 0.1 mM or less had an adverse effect on budesonide stability at accelerated temperatures (40° C.).

Example 9

A composition containing fluticasone 17-propionate was prepared using 0.01 M citrate buffer, pH 5.0, as an aqueous phase. Fluticasone 17-propionate (27.5 mg) was dissolved in 9.9725 g of a 2:1 w/w mixture of TPGS and polyoxyethylene glycol 400 by stirring for 1 hour at 60° C. The hot concentrate was diluted (1:25 wt/wt) with 0.01 M citrate buffer, pH 5, containing 1.6% propylene glycol for tonicity adjustment, by mixing for 20 minutes at 60° C. The final transparent solution was sterilized by passing it through a 0.2 micron sterile filter and filled into sterile plastic low density polyethylene vials. The composition of the formulation is given in the following table.

| Component | Weight Percent Concentrate mixture | Wt/Wt Percent After 1:25 Dilution |
| --- | --- | --- |
| TPGS | 66.487 | 2.6595 |
| Polyethylene glycol 400 | 33.238 | 1.3295 |
| Fluticasone 17-propionate | 0.275 | 0.011 |
| Propylene glycol | — | 1.536 |
| 0.01 M citrate buffer, pH 5 | — | 94.464 |

This composition is suitable for delivery of fluticasone 17-propionate by oral inhalation using a nebulizer.

Example 10

The following fluticasone composition is suitable for nasal administration and contains benzalkonium chloride and disodium edetate as preservatives and sodium chloride as an osmolality adjuster.

The amount of 0.4 g of Fluticasone 17-propionate was added to 79.6 g of melted TPGS and a mixture was stirred at 60° C. until homogeneous (approximately 1 hr). The concentrate was diluted (1:10 wt/wt) with an aqueous phase consisting of 0.01 M citrate buffer, sodium chloride, benzalkonium chloride and disodium edetate. The mixture was stirred at 60° C. for 20 minutes (until homogeneous). The composition of the formulation is given-in the following table.

| Component | Weight Percent Concentrate mixture | Wt/Wt Percent After 1:10 Dilution |
|---|---|---|
| TPGS | 99.5 | 9.950 |
| Fluticasone 17-propionate | 0.5 | 0.050 |
| Sodium chloride | — | 0.612 |
| Benzalkonium chloride | — | 0.020 |
| Disodium edetate | — | 0.050 |
| 0.01 M citrate buffer, pH 5 | — | 89.318 |

Example 11

This example contains two corticosteroid compositions that form oil-in-water microemulsions after dilution of the concentrate with an aqueous phase.

Fluticasone 17-propionate (38.5 mg) was dissolved in 9.9615 g of a mixture of TPGS-Captex 300 (9:1 by weight) by stirring for 1 hour at 60° C. The concentrate was diluted (1:35 wt/wt) with 0.01 M citrate buffer containing 1.8% propylene glycol as an osmolality adjuster by stirring for 10 minutes at 60° C. The composition of the final transparent formulation is given in the following table.

| Component | Weight Percent Concentrate mixture | Wt/Wt Percent After 1:35 Dilution |
|---|---|---|
| TPGS | 89.6535 | 2.5623 |
| Captex 300 | 9.9615 | 0.2847 |
| Fluticasone 17-propionate | 0.385 | 0.011 |
| Propylene glycol | — | 1.7486 |
| 0.01 M citrate buffer, pH 5 | — | 95.3934 |

Captex 300 is a mixture of triglycerides of medium chain fatty acids. This composition is suitable for inhaled oral delivery of fluticasone 17-propionate using a nebulizer.

Example 12

This oil-in-water microemulsion composition contains a concentration of budesonide that is suitable for nasal administration. The following mixture was prepared and used as a nonaqueous phase:

| | Weight percentage |
|---|---|
| TPGS | 89.1 |
| Captex 300 | 0.9 |
| Capmul MCM | 10 |

Budesonide (0.016 g) was dissolved in the above nonaqueous phase (1.984 g) by stirring at 55° C. for 20 minutes. The prepared concentrate was then diluted (1:16) with 0.02 M citrate buffer, pH 5, containing sodium chloride and benzalkonium chloride. An optically transparent oil-in-water microemulsion was formed. The composition of the formulation is given in the following table. Capmul MCM is a mixture of mono- and di-glycerides of medium chain fatty acids.

| Component | Weight Percent Concentrate mixture | Wt/Wt Percent After 1:16 Dilution |
|---|---|---|
| TPGS | 88.3872 | 5.5242 |
| Captex 300 | 9.9200 | 0.6200 |
| Capmul MCM | 0.8928 | 0.0558 |
| Budesonide | 0.8000 | 0.0500 |
| Sodium chloride | — | 0.6500 |
| Benzalkonium chloride | — | 0.0200 |
| 0.02 M citrate buffer, pH 5 | — | 93.0800 |

What is claimed is:

1. A composition suitable for administering a therapeutic dose of a corticosteroid which is budesonide, to the respiratory tract, consisting of:
    (a) from about 5 µg/ml to about 5 mg/ml of the corticosteroid in dissolved form;
    (b) from about 0.1 to about 20 percent by weight of a pharmaceutically acceptable, high-HLB surfactant component, wherein the HLB of the surfactants present in the high-HLB surfactant component is greater than about 10, and wherein the high-HLB surfactant component comprises at least 50% by weight of an ethoxylated derivative of vitamin E, wherein said ethoxylated derivative of vitamin E is the sole vitamin E component of the composition; and
    (c) at least about 70 weight percent aqueous phase.

2. The composition of claim 1 wherein the high-HLB surfactant component comprises at least 50% by weight tocopheryl polyethylene glycol 1000 succinate.

3. A composition suitable for administering a therapeutic dose of a corticosteroid which is budesonide, to the respiratory tract, consisting of:
    (a) from about 5 µg/ml to about 5 mg/ml of the corticosteroid in dissolved form;
    (b) from about 0.1 to about 20 percent by weight of a high-HLB surfactant component wherein the HLB of the surfactants present in the high-HLB surfactant component is greater than about 10, and wherein the high-HLB surfactant component comprises at least 50% by weight of an ethoxylated derivative of vitamin E, wherein said ethoxylated derivative of vitamin E is the sole vitamin E component of the composition;
    (c) at least about 70 weight percent aqueous phase; and
    (d) from about 0.1 to about 20 percent by weight of a pharmaceutically acceptable cosolvent comprising propylene glycol, polyethylene glycol having a molecular weight between about 200 and 4000, glycerol, ethoxydiglycol, glycofurol, and ethanol, or a combination thereof.

4. The composition of claim 3 wherein the high-HLB surfactant component comprises at least 90% by weight of an ethoxylated derivative of vitamin E.

5. The composition of claim 3 wherein the high-HLB surfactant component comprises at least 75% by weight of an ethoxylated derivative of vitamin E.

6. A composition suitable for administering a therapeutic dose of a corticosteroid which is budesonide, to the respiratory tract, consisting of:
    (a) from about 5 µg/ml to about 5 mg/ml of the corticosteroid in dissolved form;
    (b) from about 0.1 to about 20 percent by weight of a high-HLB surfactant component wherein the HLB of the surfactants present in the high-HLB surfactant component is greater than about 10, and wherein the high-HLB surfactant component comprises at least 50% by weight of an ethoxylated derivative of vitamin E, wherein said ethoxylated derivative of vitamin E is the sole vitamin E component of the composition;
(c) at least about 70 weight percent aqueous phase; and
(d) from about 0.1 to about 3 percent by weight of a low HLB surfactant having an HLB below about 8.

7. A composition suitable for administering a therapeutic dose of a corticosteroid which is budesonide, to the respiratory tract, consisting of:
(a) from about 5 μg/ml to about 5 mg/ml of the corticosteroid in dissolved form;
(b) from about 0.1 to about 20 percent by weight of a high-HLB surfactant component wherein the HLB of the surfactants present in the high-HLB surfactant component is greater than about 10, and wherein the high-HLB surfactant component comprises at least 50% by weight of an ethoxylated derivative of vitamin E, wherein said ethoxylated derivative of vitamin E is the sole vitamin E component of the composition;
(c) at least about 70 weight percent aqueous phase; and
(d) from about 0.1 to about 3 percent by weight of an oil.

8. The composition of claim 1 wherein the ethoxylated derivative of vitamin E comprises at least 75% by weight of the high-HLB surfactant component.

9. The composition of claim 1 wherein the ethoxylated derivative of vitamin E comprises at least 90% by weight of the high-HLB surfactant component.

10. The composition of claim 1 wherein the high-HLB surfactant component comprises at least 75% by weight tocopheryl polyethylene glycol 1000 succinate.

11. The composition of claim 1 wherein the high-HLB surfactant component comprises at least 90% by weight tocopheryl polyethylene glycol 1000 succinate.

12. The composition of claim 3 wherein the high-HLB surfactant component comprises at least 75% by weight tocopheryl polyethylene glycol 1000 succinate.

13. The composition of claim 3 wherein the high-HLB surfactant component comprises at least 90% by weight tocopheryl polyethylene glycol 1000 succinate.

* * * * *